(12) United States Patent
Dong

(10) Patent No.: US 11,325,346 B2
(45) Date of Patent: May 10, 2022

(54) PROTECTIVE FABRIC AND PROTECTIVE PRODUCT

(71) Applicant: Senturion+ LLC, Honolulu, HI (US)

(72) Inventor: Liangjie Dong, Honolulu, HI (US)

(73) Assignee: Senturion+ LLC, Honolulu, HI (US)

( * ) Notice: Subject to any disclaimer, the term of this patent is extended or adjusted under 35 U.S.C. 154(b) by 32 days.

(21) Appl. No.: 17/067,915

(22) Filed: Oct. 12, 2020

(65) Prior Publication Data
US 2022/0111615 A1    Apr. 14, 2022

(51) Int. Cl.
*B01D 53/02* (2006.01)
*B32B 5/30* (2006.01)
(Continued)

(52) U.S. Cl.
CPC ........... *B32B 5/30* (2013.01); *A41D 13/1192* (2013.01); *A61L 9/014* (2013.01); *B01D 39/1623* (2013.01); *B01D 39/2079* (2013.01); *B01J 20/0233* (2013.01); *B01J 20/12* (2013.01); *B01J 20/28028* (2013.01); *B01J 20/28038* (2013.01); *B01J 20/3021* (2013.01); *B01J 20/3078* (2013.01); *B01J 20/3204* (2013.01); *B01J 20/3236* (2013.01); *B01J 20/3293* (2013.01); *B32B 5/022* (2013.01); *B32B 5/16* (2013.01); *B32B 5/24* (2013.01); *B32B 18/00* (2013.01); *A61L 2101/28* (2020.08); *A61L 2209/14* (2013.01); *A62B 18/02* (2013.01);
(Continued)

(58) Field of Classification Search
CPC ... B23B 5/30; B41D 13/1192; B01D 39/1623; B01D 39/2079; B01D 2239/0407; B01D 2239/0442; B01D 2239/0618; B01D 2239/065; B01D 2239/10; B01J 20/0233; B01J 20/12; B01J 20/28028; B01J 20/3021; B01J 20/3078; B01J 20/3204; B01J 20/3236; B01J 20/3293; B32B 5/022; B32B 5/16; B32B 5/24
See application file for complete search history.

(56) References Cited

U.S. PATENT DOCUMENTS

2009/0127208 A1\*  5/2009  Berkowitz ............... B09C 1/08
                                                              210/749
2017/0341054 A1\*  11/2017  Glover ................... D21H 21/28
(Continued)

FOREIGN PATENT DOCUMENTS

CN        2017-11435 H  *  2/2017

OTHER PUBLICATIONS

Translation of CN106376992 A, Chen (Year: 2017).*

*Primary Examiner* — Christopher P Jones
(74) *Attorney, Agent, or Firm* — Yong Chen

(57) ABSTRACT

A protective fabric which includes at least one structural layer and a ceramic composite material layer fixed to the at least one structural layer, is provided. The structural layer can include a non-woven material made from or containing synthetic fibers. The ceramic composite material layer is formed of ceramic composite material powder which includes a ceramic carrier, and iron-silver crystals containing zero-valent iron and zero-valent silver supported on the ceramic carrier. The protective fabric is effective for removing VOCs, suppressing bacterial growth, and filtering or inactivating virus, such as SARS-CoV-2 virus. Protective products or articles incorporating the protective fabric are also provided.

20 Claims, 6 Drawing Sheets

(51) Int. Cl.
*B32B 5/16* (2006.01)
*A41D 13/11* (2006.01)
*B32B 18/00* (2006.01)
*B32B 5/02* (2006.01)
*A61L 9/014* (2006.01)
*B01J 20/02* (2006.01)
*B01J 20/12* (2006.01)
*B01J 20/28* (2006.01)
*B01J 20/32* (2006.01)
*B01J 20/30* (2006.01)
*B01D 39/16* (2006.01)
*B01D 39/20* (2006.01)
*B32B 5/24* (2006.01)
*A61L 101/28* (2006.01)
*A62B 23/02* (2006.01)
*A62B 18/02* (2006.01)

(52) U.S. Cl.
CPC ...... *A62B 23/02* (2013.01); *B01D 2239/0407* (2013.01); *B01D 2239/0442* (2013.01); *B01D 2239/065* (2013.01); *B01D 2239/0618* (2013.01); *B01D 2239/10* (2013.01); *B32B 2250/40* (2013.01); *B32B 2262/0253* (2013.01); *B32B 2264/107* (2013.01); *B32B 2571/00* (2013.01)

(56) References Cited

U.S. PATENT DOCUMENTS

2019/0106337 A1\* 4/2019 Dong ................ B01J 20/28085
2020/0384530 A1\* 12/2020 Sethi ...................... B22F 1/007

\* cited by examiner

PROTECTIVE FABRIC AND PROTECTIVE PRODUCT

TECHNICAL FIELD

The invention relates to a protective fabric and a protective product incorporating the protective fabric. The protective product can be used as protective clothing, protective cover, mask, curtain, wall cloth, or a filtration medium for an air filtering, ventilation or circulation device or system.

BACKGROUND

In radiological medicine labs and cleanrooms, fabrics of curtains and wall coverings, clothing materials for staff, and non-woven filter cloths for fresh air systems are usually required to be antibacterial, and be able to filter bacteria and absorb volatile radioactive iodine aerosol, volatile organic compounds (VOCs), etc. Protective equipment such as masks may also have performance requirements of adsorption and fixation of mercury in haze or smog, and filtration of sulfur dioxide.

Lead materials have been widely used for blocking β and γ ray radiation. However, lead materials are heavy and can cause serious environmental pollution.

For current face masks made of cloth or nonwoven fabric materials, bacteria growth can be a problem. When worn by a wearer, especially for prolonged use, the increase of humidity and temperature within the mask can facilitate the growth of bacteria, leading to unpleasant odors and health risks for the wearer. To suppress the bacteria growth, a mask needs to have good gas permeability. However, high gas permeability does not favor filtration of VOC or other undesirable contaminants or pollutants in the air. In addition, common mask material cannot effectively filter virus.

SUMMARY OF THE INVENTION

In view of the above-mentioned issues in the prior art, an object of the present invention is to provide a protective fabric and protective products or articles incorporating the protective fabric. The protective fabric can be soft and flexible, can block radiation, and has antibacterial and filtering properties. The protective product can be a protective clothing, protective cover, face mask (or respirator), curtain, wall covering, or a filtration medium for an air filtering, ventilation or circulation device or system, or the like.

In one aspect, the present disclosure provides a protective fabric comprising at least one structural layer comprising fibrous materials, and a ceramic composite material layer fixed to the at least one structural layer. The ceramic composite material layer is formed of ceramic composite material powder comprising a ceramic carrier and iron-silver crystals supported on the ceramic carrier, where the iron-silver crystals comprising zero-valent iron and zero-valent silver.

In some embodiments of the fabric, the weight ratio of the zero-valent silver and zero-valent iron can be 0.22:1 to 0.44:1.

In some embodiments of the fabric, the ceramic composite material powder has a particle size of greater than 325 meshes. In some embodiment, the ceramic composite material powder has a pH not less than 10, e.g., has a pH of between 10 and 12.

In some embodiments, the ceramic composite material powder is prepared by (a) calcining a mixture containing ceramic raw material, silver citrate, and ferrous citrate under an anoxic atmosphere to thereby obtain a calcined product; and (b) grinding the calcined product to obtain the ceramic composite material powder. In certain of these embodiments, the ceramic raw material comprises one of gibbsite and alkaline sodium bentonite. In certain of these embodiments, the ceramic raw material comprises both gibbsite and alkaline sodium bentonite.

In some embodiments, the ceramic composite material powder is prepared by the following steps: mixing a ceramic raw material and water-soluble starch uniformly, and further mixing with an aqueous solution containing a mixture of silver citrate and ferrous citrate to produce a first mixture; granulating the first mixture to produce a first granule; drying, calcining and cooling the first granule in a nitrogen atmosphere to produce a second granule; and grinding the second granule. In certain of these embodiments, the ceramic raw material comprises one of gibbsite and alkaline sodium bentonite. In certain of these embodiments, the ceramic raw material comprises both gibbsite and alkaline sodium bentonite.

In some embodiments, the at least one structural layer comprises a non-woven material comprising synthetic fibers.

In some embodiments of the fabric, the at least one structural layer comprises two structural layers each comprising fibrous materials, and the ceramic composite material layer is disposed between the two structural layers. In some embodiments, each of the two structural layers comprises a non-woven material comprising synthetic fibers.

In some embodiments of the fabric, the thickness of the ceramic composite material layer is between about 0.05 mm and about 3.0 mm. In some embodiments of the fabric, the thickness of the protective fabric is between about 0.1 mm and about 10 mm.

The word "about" as used in this application in association with a numeric value or a numeric range mean "approximately" and refers to a result that can be obtained within a tolerance and the skilled person knows how to obtain the tolerance, for example, ±10% of the given value or range.

The protective fabric of the present invention is effective for removing or inactivating a virus, such as a corona virus (e.g., SARS-CoV-2 virus), suppressing bacterial growth, removing VOCs in the air, $SO_2$, and iodine vapor (such as radioactive $^{131}I$ vapor).

In another aspect, the present disclosure provides a protective product comprising a functional body with protective functions, where the functional body is made of or comprise the protective fabric described herein. The protective product can be a protective clothing, a protective cover, a face mask or respirator (covering a person's nose and/or mouth), a curtain, a wall cloth, a filtration medium for an air filtering/ventilation/circulation device or system, or the like. The protective product can be directly worn by a person, or placed as barrier material between a person or the living/working space of the person, and source of undesired contaminants.

In another aspect, the present disclosure provides a method of reducing the harm of air-borne contaminants (such as SARS-CoV-2 virus, VOCs, and other contaminants or pollutants that may pose a health risk to a person). In using or wearing the protective product described herein, such as a face mask, the protective fabric is positioned as a barrier between the air with contaminants and a part of the person's body that requires protection, such as his or her nose and/or mouth.

In a further aspect, the present disclosure provides the ceramic composite material powder, and methods of making the ceramic composite material powder as described herein.

In a further aspect, the present disclosure provides methods of making the protective fabric described herein.

DETAILED DESCRIPTION

Figure 1A:
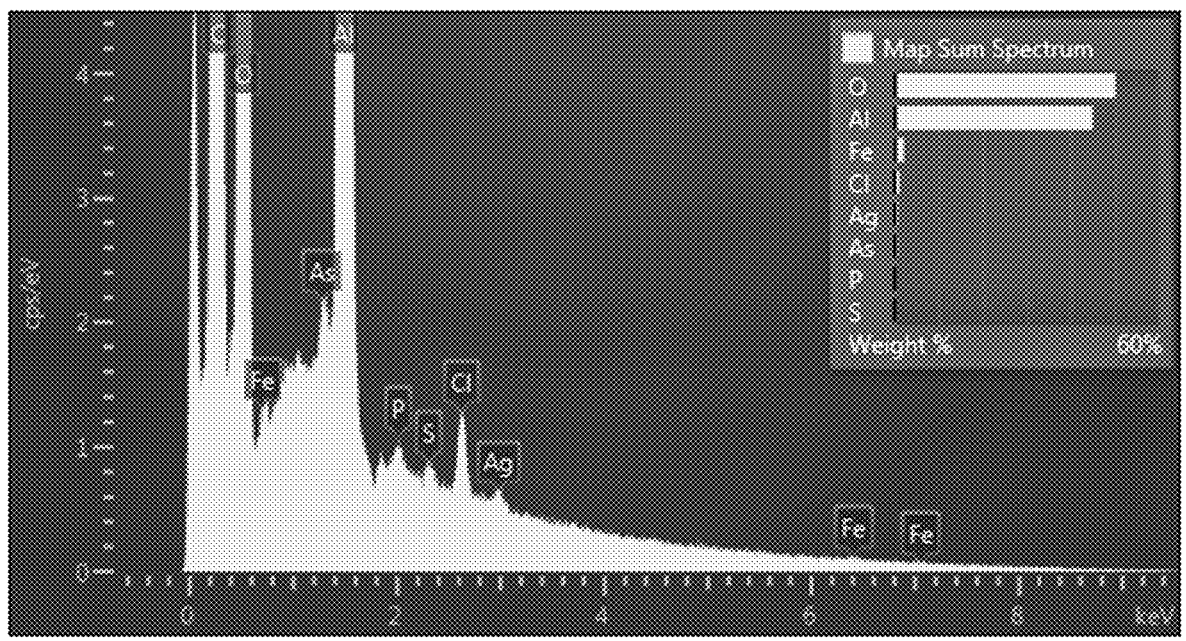
FIG. 1a is an elemental spectrogram of a ceramic composite material powder obtained according to Example 1 of the present disclosure.

Certain embodiments of the present invention are described in detail below in conjunction with the accompanying drawings, so that the advantages and features of the present invention can be more easily understood by those skilled in the art.

In one aspect, the present disclosure provides a protective fabric comprising at least one structural layer comprising fibrous materials, and a ceramic composite material layer fixed to the at least one structural layer. It is understood that one structural layer may include several sub-layers. The ceramic composite material layer is formed of ceramic composite material powder comprising a ceramic carrier and iron-silver crystals supported on the ceramic carrier, where the iron-silver crystals comprising zero-valent iron and zero-valent silver.

As used herein, "iron-silver crystals" (or "silver-iron crystals") generally refer to crystal material in the ceramic composite material powder that comprise either or both of zero-valent iron and zero-valent silver. In some embodiments, the iron-silver crystals comprise co-crystals of zero-valent iron and zero-valent silver, as well as crystals containing only zero-valent iron and crystals containing only zero-valent silver. The co-crystals of zero-valent iron and zero-valent silver can account for from about 15% to about 85% by weight in the total amount of all iron-silver crystals.

In some embodiments of the fabric, the weight ratio of the zero-valent silver to zero-valent iron in the iron-silver crystals is 0.22:1 to 0.44:1.

The ceramic carrier is generally porous. The iron-silver crystals can be on the surface of the ceramic carrier and in the pores of the ceramic carrier.

In some embodiments of the fabric, the ceramic composite material powder has a particle size of 325 mesh or a greater mesh number. In some embodiment, the ceramic composite material powder has a pH not less than 10, e.g., between 10 and 12.

In some embodiments, the ceramic composite material powder is prepared by (a) calcining a mixture containing ceramic raw material, silver citrate, and ferrous citrate under an anoxic atmosphere to thereby obtain a calcined product; and (b) grinding the calcined product to obtain the ceramic composite material powder. In certain of these embodiments, the ceramic raw material comprises one of gibbsite and alkaline sodium bentonite. In certain of these embodiments, the ceramic raw material comprises both gibbsite and alkaline sodium bentonite.

In some embodiments, the ceramic composite material powder is prepared by the following procedure: mixing a ceramic raw material and water-soluble starch uniformly, and further mixing with an aqueous solution containing a mixture of silver citrate and ferrous citrate to produce a first mixture; granulating the first mixture to produce a first granule; drying, calcining and cooling the first granule in a nitrogen atmosphere to produce a second granule; and grinding the second granule to obtain the ceramic composite material powder. In certain of these embodiments, the ceramic raw material comprises one of gibbsite and alkaline sodium bentonite. In certain of these embodiments, the ceramic raw material comprises both gibbsite and alkaline sodium bentonite. In certain of these embodiments, drying the first granule can be performed at a temperature between 80° C. to 150° C., e.g., at about 120° C., with nitrogen protection, and the follow-on calcination can be performed (also with nitrogen protection) with a temperature ramping up to a target elevated temperature between 300° C. and 850° C., e.g., about 800° C., e.g., at a ramping rate of 5° C./min, and holding the granule at the target temperature for an extended period of time, e.g., about 2-8 hours, e.g., about 4 hours. The calcined granule can be cooled down naturally (also in anoxic atmosphere), and then ground to powder with a pulverizer to reach desired particle size, e.g., smaller than one that can pass a designated sieve of 325 mesh or of a greater mesh number, or smaller than 0.044 mm, for subsequent use.

As used herein, the word "powder" and "granule" in singular form refer to a collection of particles in the form of powder or granule.

In some embodiments of the fabric, the at least one structural layer comprises two structural layers each comprising fibrous materials, where the ceramic composite material layer is disposed between the two structural layers. The structural layer or layers can be made from a non-woven fibrous material or woven fibrous material. The fibers in the structural layer can be natural cellulose fibers, which can be cotton fibers or fibers derived from other plants, or synthetic fibers such as polyethylene, polypropylene, polyesters, polyamides, acrylics, etc., or a mixture of natural fibers and synthetic fibers. The ceramic composite material layer can be thermally bonded on the structural layer by heat bonding material, e.g., a thermoplastic resin, such as a PE resin.

Manufacture of the protective fabric can be accomplished by a procedure similar to that for making nonwoven fabric. For example, natural fibers or synthetic fibers can be laid on a surface, and then the ceramic composite material powder described herein is laid on top of the laid fibers with predetermined density (g/m$^2$, or gsm). Another layer of fibers is laid on top of the ceramic composite material powder. The layered structure is compacted while being subject heat treatment, e.g., by heated rollers, for the bonding of the fibers and the tight integration of the layers, as well as for removing moisture. The finished fabric material is sheet-like, and can be flexible and foldable like a cloth. Alternatively, non-woven material in the form of sheet can be used directly and compacted with the ceramic composite material powder layer. The structural layer(s) provides the strength and structural integrity for the fabric as a whole, while the ceramic composite material layer provides the filtering and other functions described herein.

In some embodiments of the fabric, the thickness of the ceramic composite material layer is between about 0.05 mm and about 3.0 mm. In some embodiments of the fabric, the thickness of the protective fabric is between about 0.1 mm and about 10 mm.

The protective fabric of the present disclosure, while retaining a soft and flexible texture, can effectively block middle and low-intensity beta and gamma rays. In contrast to conventional radiation protective apparel including layer made from lead (Pb), the fabric of the present disclosure offers a lightweight and more comfortable alternative. The protective fabric of the present disclosure can absorb iodine vapor in the air and prevent/reduce the harm of radioactive iodine to the human body. The protective fabric can also adsorb and chemically fix the sulfur dioxide, overcoming the shortcomings of activated carbon which can only physically adsorb contaminants and is easily saturated. Without resorting to additional chemical agents, the protective fabric of the present disclosure can filter bacterial and suppress bacterial growth, and can filter out, kill or inactivate viruses, such as SARS-CoV-2 virus. The multiple combined benefits of the fabric make it a desirable protective material for personal protective equipment and protective material for protecting a workspace in hospitals, laboratories and other settings. The protective product incorporating the protective fabric is suitable for use as antibacterial and/or radiation protective clothing, protective covers, masks, curtains and wall cloths, filter materials for radiological medicine or cleanrooms, etc.

EXAMPLES

The examples below are intended to be purely exemplary of the invention and should therefore not be considered to limit the invention in any way.

Example 1. Preparation of Ceramic Composite Material Powder

Raw materials: gibbsite (1200 mesh), alkaline sodium bentonite (1200 mesh), water-soluble starch (1200 mesh); silver citrate (analytical purity); ferrous citrate (analytical purity).

1. Mixing and granulation: three different powder of gibbsite, alkaline sodium bentonite, and water-soluble starch were mixed in the mixer at a weight ratio of 1:1:1 (3 minutes, 5000 revolutions/min). The mixture was added with an aqueous solution containing 0.5% silver citrate and 3% ferrous citrate. The resulting mixture was processed to form a first granule having 0.5-1 mm in diameter;

2. Drying the first granule at 120° C., with nitrogen protection;

3. Calcination and cooling in nitrogen atmosphere: the pre-dried granule was calcined with a temperature ramp at a heating rate 5° C./min to 800° C., then held at 800° C. for 4 hours, and then cooled naturally, all with nitrogen protection.

The cooled granule was ground by a pulverizer to reach a particle size smaller than 325 mesh (or a greater mesh number) for later use.

Figure 1B:
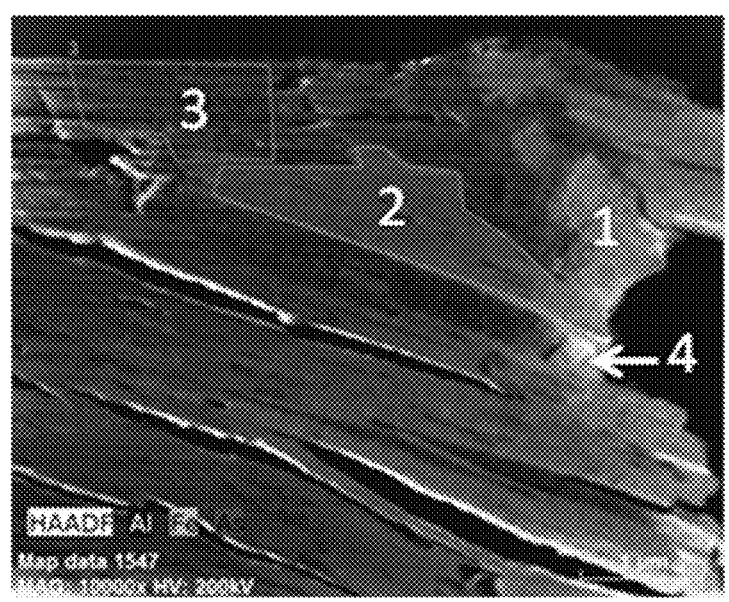
FIG. 1b is an electron micrograph of a specimen of a ceramic composite material powder obtained according to Example 1 of the present disclosure, with four areas marked for elemental analysis.

The prepared ceramic composite material powder has the following properties:
Burning residue content: 26±2%;
Water content: ≤3%;
Surface cleanliness: dust ≤1 g/m²;

The ceramic composite material powder prepared above was sliced and tested by scanning transmission electron microscope (Titan ChemiSTEM) and then SEM and EDS. The spectrogram of the imaging area is shown in FIG. 1a. FIG. 1b show electron microscopy image of a specimen of the ceramic composite material powder, with 4 test areas marked. Table 1 shows the elemental analysis results of marked areas 1, 2, 3, and 4 in FIG. 1b.

TABLE 1

| norm. at. % | Area 1 | Area 2 | Area 3 | Area 4 |
|---|---|---|---|---|
| O | 48.8 | 51.5 | 62.8 | 45.2 |
| Al | 49.8 | 47.7 | 36.2 | 52.3 |
| Fe | 1.1 | 0.6 | 0.8 | 1.8 |
| Ag | 0.2 | 0.3 | 0.2 | 0.7 |
| Total | 100.0 | 100.0 | 100.0 | 100.0 |
| Ag/Al | 0.005 | 0.005 | 0.007 | 0.013 |
| Ag/Fe | 0.22 | 0.44 | 0.31 | 0.38 |

The iron-silver crystals include co-crystals of zero-valent iron and zero-valent silver, which can account for about 15% to about 85% of the total amount of silver-iron crystals containing Ag and/or Fe. The silver and iron co-crystals can effectively block γ-rays. It was found that the powder material has good γ-rays blocking capacity at a Ag/Fe ratio of 0.22:1 to 0.44:1, and reaches the best γ-rays blocking capacity at a Ag/Fe ratio of about 0.33:1. It is noted that in the absence of silver, γ-rays cannot be absorbed and blocked by ceramic composite material with Fe crystals alone.

Figure 2:
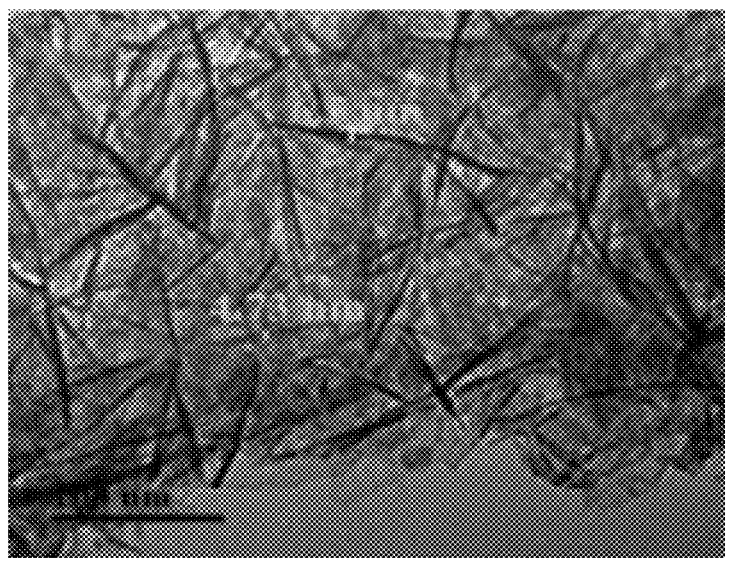
FIG. 2 is a electron micrograph showing needle-like iron-silver crystals in a ceramic composite material powder according to Example 1 of the present disclosure.

FIG. 2 shows needle-shaped iron-silver crystals in the ceramic composite material powder, observed both on the surface of the ceramic carrier, as well as in the pores of the ceramic carrier. The presence of alkaline sodium bentonite causes the surface pH of the ceramic powder to be ≥10, under which condition bacterial growth is inhibited. The surface of the ceramic material is coated with dense needle-shaped silver-iron crystals, which can hook, entangle or otherwise impede bacteria. The silver-iron crystals in the pores of the ceramic material may cut, slice or otherwise damage a virus when the virus (generally less than 100 nanometers) passes through. When sulfur dioxide gas passes through the ceramic composite material, it reacts with zero-valent iron and get fixated or immobilized in the ceramic material.

Example 2. Preparation of a Protective Fabric of the Present Invention

Raw Material
1. A non-woven (medical grade) polypropylene SMMS (4 layers, spunbond+meltblown+meltblown+spunbond) fabric, density 55 g/m², used as top and bottom structural layers.
2. The ceramic composite material powder prepared in Example 1.
3. Bonding material: low melting point PE powder (particle size smaller than 325 mesh).

Process of Making the Protective Fabric

Figure 3:
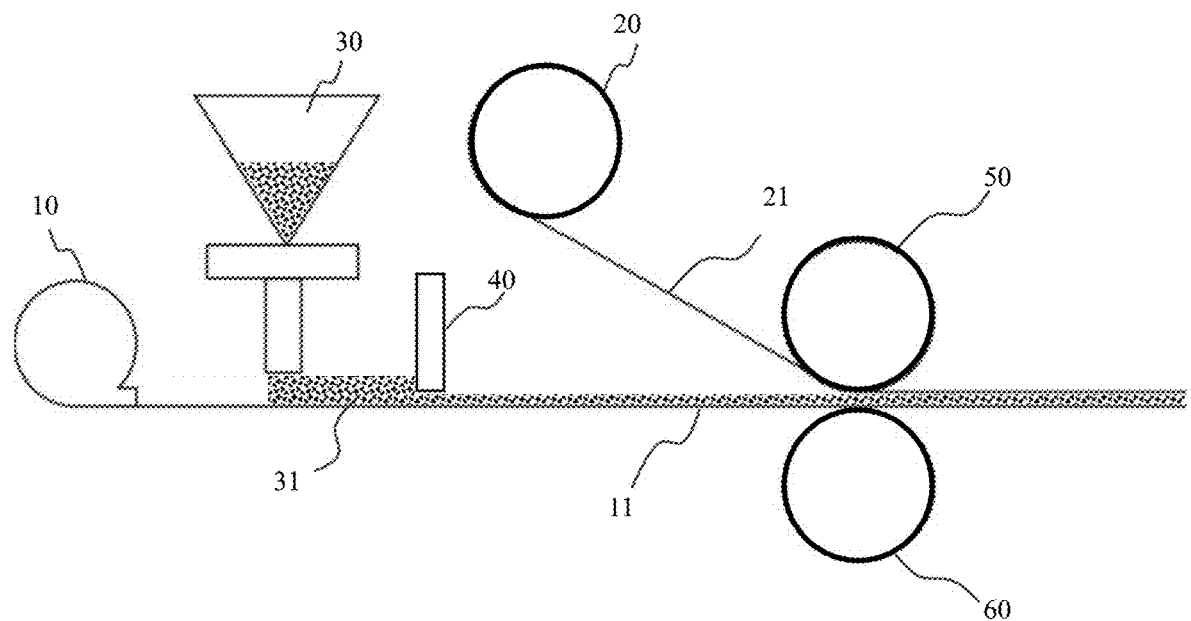
FIG. 3 is a schematic diagram of the preparation of a protective fabric according to an embodiment of the present invention.

As shown in the schematic diagram of FIG. 3, the bottom non-woven structural layer 11 (supplied by supply roller 10), top non-woven structural layer 21 (supplied by supply roller 20), and ceramic composite material powder 31, provided from the supply funnel 30 and deposited on top of the bottom non-woven structural layer 11 (and its thickness/amount adjusted by the block 40) are compressed and laminated (by calendar rollers 50 and 60 at a temperature of about 150° C.) to form a sandwich-like layered structure, with the ceramic composite material powder disposed between the top and bottom non-woven layers. Thermal bonding PE resin powder in the amount of 1-3 wt % of the total protective fabric material was used in the process to improve the adhesion between the ceramic composite material powder layer and the non-woven structural layers.

Example 3: Performance Test of Different Materials

The protective fabric prepared in Example 2 was used to make a face mask, and the following tests were performed.
Antibacterial Test on the Surface of Mask Material Test materials: the protective fabric prepared in Example 2 (denoted as MN), 3M 9041V N90 activated carbon interlayer mask material (denoted as 3M), Honeywell H930 KN95 non-interlayer haze and dust mask material (denoted as HW), and a PET fabric material (denoted as PET). The 3M and HW material utilize static electric charge to facilitate capture of small particles in the air. The activated carbon embedded in the 3M material also adsorbs or traps contaminants with its large surface area.

Test conditions: Humidity 65%, temperature 28° C., inoculation concentration 10000/ml, 7 ml $E.\ coli$ bacteria containing solution was sprayed once on the test material, and the time-profile of the surface bacteria concentration was obtained.

Figure 4:
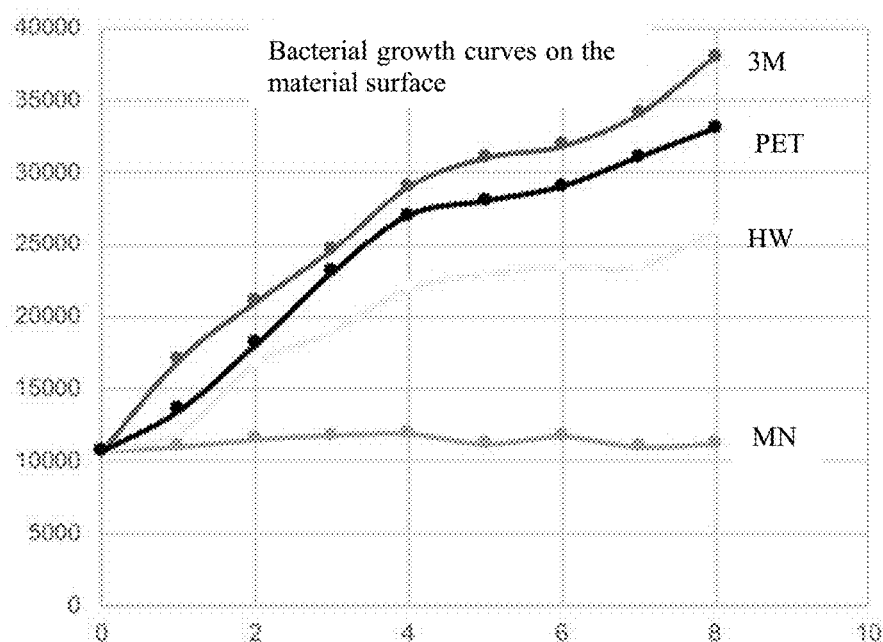
FIG. 4 shows bacterial growth curves of on the surface of a fabric material according to an embodiment of the present invention.

Test results: FIG. 4 shows bacterial growth curves of these tested materials under the same condition. It can be seen that the protective fabric of the present invention has better antibacterial performance than the other materials when used as a mask material.
Nebulized Bacteria Solution Filtration Test
Testing Method:
1. 1 ml of bacteria containing aqueous solution ($E.\ coli$) with a concentration of 11000/ml was nebulized into a 50 ml pressure tank, and then flowed at a constant pressure of 5.5 psi to each of the above four materials (MN, 3M, HW, PET) respectively covering an air chamber;
2. Bacterial concentration on both sides (the front surface that is directly exposed to the nebulized bacterial solution, and the opposing back surface) as well as the interior of each of the test material was tested within 30 minutes;
3. After 24 hours bacteria at the bottom of the air chamber (after filtration) was counted to calculate the filtration efficiency;
4. Electron microscopy was used to detect bacteria adhesion in the front surface, interior, and back surface of the materials.

Data for bacteria distribution after filtration and the calculated filtration efficiency are shown in Table 2.

TABLE 2

| Test Material | MN | 3M | HW | PET |
| --- | --- | --- | --- | --- |
| Nebulized liquid bacteria concentration | 10700 | 10700 | 10700 | 10700 |
| Front surface | 2700 | 4700 | 7800 | 3500 |
| Interior | 6500 | 4500 | 1001 | 3800 |
| Back surface | 59 | 1000 | 890 | 2100 |

TABLE 2-continued

| Test Material | MN | 3M | HW | PET |
| --- | --- | --- | --- | --- |
| Concentration (bacteria count in air chamber) | 125 | 2300 | 1200 | 3200 |
| Filtration efficiency | 98.83% | 78.50% | 88.79% | 70.09% |

It can be seen from Table 2 that the filtration efficiency of the protective fabric of the present invention is as high as 98.83%, which is better than other materials tested.

Figure 5A:
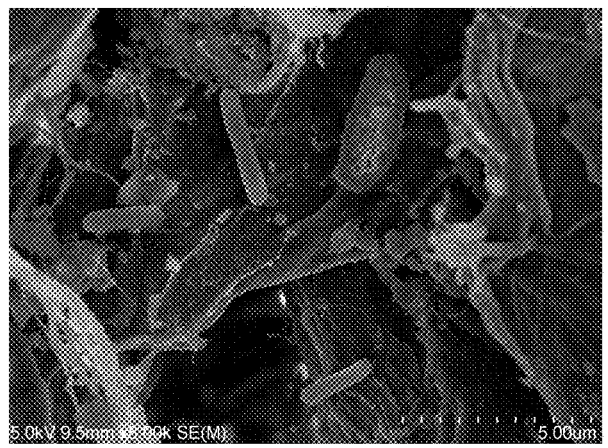
FIGS. 5a, 5b, and 5c respectively show the electron microscopy observation results of a protective fabric material according to one embodiment of the present invention along with comparative materials.
Figure 5B:
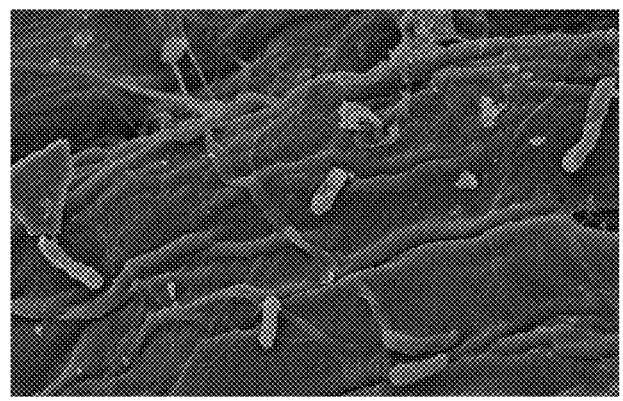
Figure 5C:
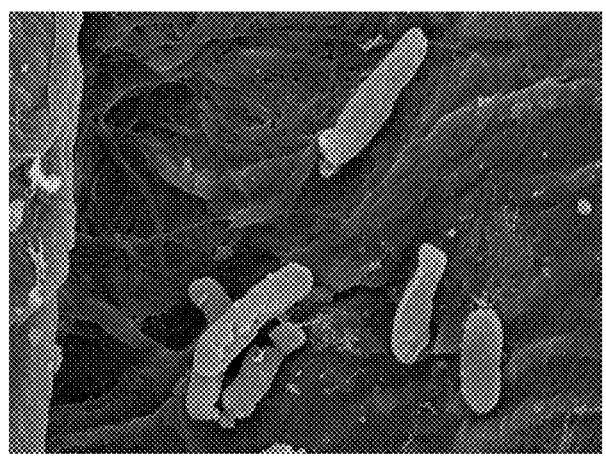

After bacterial filtration tests, samples of MN material, 3M material and HW material were observed by acidified frozen section. The electron microscope observation results of the MN material, 3M material and HW material are shown in FIGS. 5a, 5b and 5c, respectively.
VOC Filtration Test Test conditions: 16 square centimeters of each of the above four materials (MN, 3M, HW, PET) were cut, and then respectively put into a closed chamber with a filter interlayer. VOCs in argon were injected, 24 hours allowed for reaching equilibrium at a constant temperature 22° C. The filtering effects of the materials for the VOCs are shown in Table 3.

TABLE 3

| Test Material | MN | 3M | HW | PET |
| --- | --- | --- | --- | --- |
| VOC concentration (ng/m$^3$) (toluene, benzene, PAHs) | 120 | 120 | 120 | 120 |
| Equilibrium concentration through the air chamber | 25 | 11 | 58 | 76 |
| Filtration efficiency | 79.17% | 90.83% | 51.67% | 36.67% |
| Absorption capacity (mg/g) | 168 | 280 | 65 | 22 |

It can be seen from Table 3 that the protective fabric of the present invention has better filtering efficiency for VOC than other materials.
Filtering Performance for Sulfur Dioxide and Mercury Vapor Test method: dynamic balance method of closed chamber
Test conditions: sulfur dioxide test was performed at a constant temperature of 12° C., with an initial concentration of 5 ppm, a constant temperature of mercury vapor at 18° C., and an initial concentration of 5000 pg/m$^3$;

Test materials: four materials (MN, 3M, HW, and PET) as described previously.

The test results are shown in Table 4.

TABLE 4

| Test Material | MN | 3M | HW | PET |
| --- | --- | --- | --- | --- |
| Initial SO$_2$ concentration (ppm) | 5 | 5 | 5 | 5 |
| Equilibrium SO$_2$ concentration through the air chamber | 0.05 | 0.6 | 1.8 | 2.1 |
| Filtration efficiency of SO$_2$ | 98.00% | 76.00% | 28.00% | 16.00% |
| SO$_2$ absorption capacity (mg/g) | 680 | 400 | 112 | 26 |
| Hg vapor initial concentration (pg/m$^3$) | 5000 | 5000 | 5000 | 5000 |
| Concentration of Hg vapor at equilibrium | 196 | 481 | 1790 | 2100 |
| Hg removal rate (%) | 92.2 | 80.8 | 28.4 | 16.0 |

It can be seen from Table 4 that the filtration efficiency of SO$_2$ and removal rate of Hg vapor of the protective fabric of the present invention are as high as 98.00% and 92.2%, respectively, which are better than other materials.

TMV Virus Filtration Efficiency Test

The diameter of a virus is generally between 20-130 nanometers. Virus such as flu virus or coronavirus can easily get through conventional filtration materials (typical pore size >5 microns). It is difficult to simultaneously have good air permeability and good filtration efficiency for virus.

Test materials: four materials MN, 3M, HW, and PET, as described previously. The virus tested was TMV baculovirus.

Test method: The test material is used as filtration medium to seal an enclosed chamber. 2 ml of TMV virus containing aqueous solution was nebulized and sprayed into one side of the filtration medium with intermittent air jetting for 3 hours. Virus activity was determined by PCR detection.

The test results are shown in Table 5.

TABLE 5

| Test Material | MN | 3M | HW | PET |
|---|---|---|---|---|
| TMV virus concentration (ng/m$^3$) | 8220 | 8290 | 8280 | 8280 |
| Equilibrium concentration through air chamber (ng/m$^3$) | 3320 | 3010 | 4100 | 4130 |
| Virus activity (measured) | 5 | 1300 | 1900 | 3700 |
| Final filtration efficiency | 99.85% | 56.81% | 53.66% | 10.41% |

It can be seen from Table 5 that the final filtration efficiency of the protective fabric of the present invention for TMV baculovirus is as high as 99.85%, which is better than other materials.

Figure 6A:
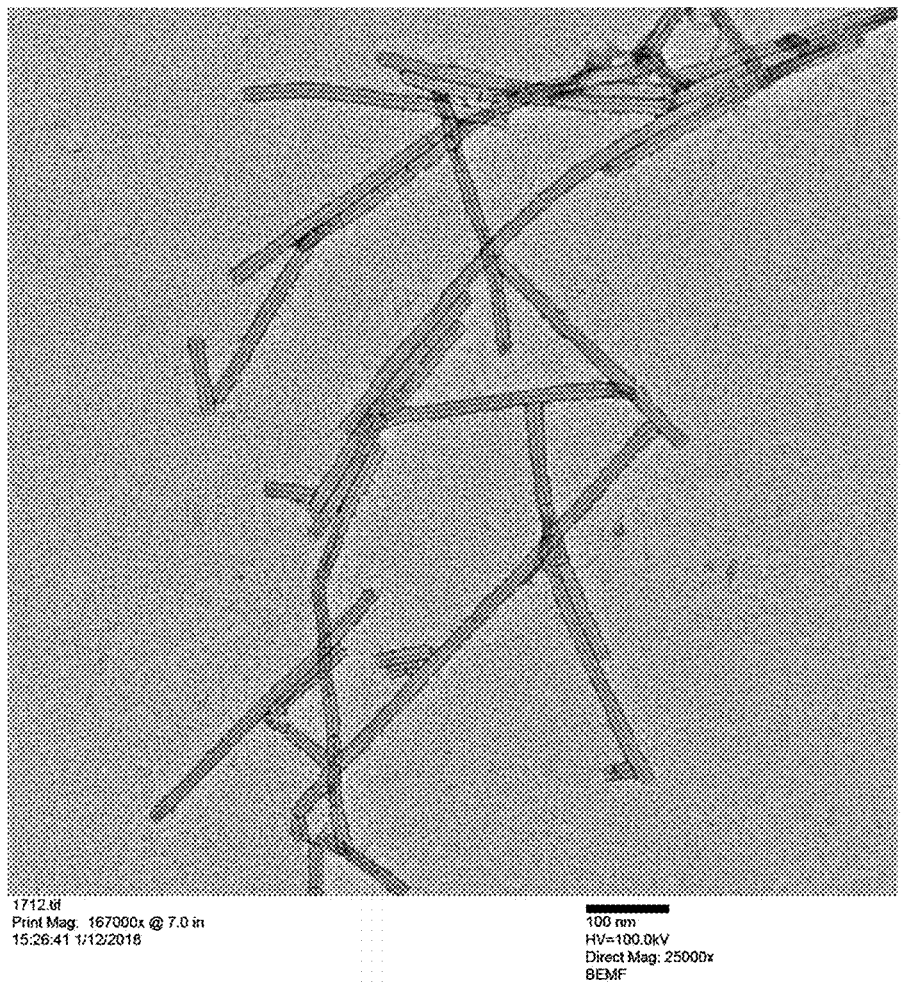
FIGS. 6a and 6b are electron micrograph showing the morphology of TMV virus before and after filtration with a protective fabric according to one embodiment of the present invention.
Figure 6B:
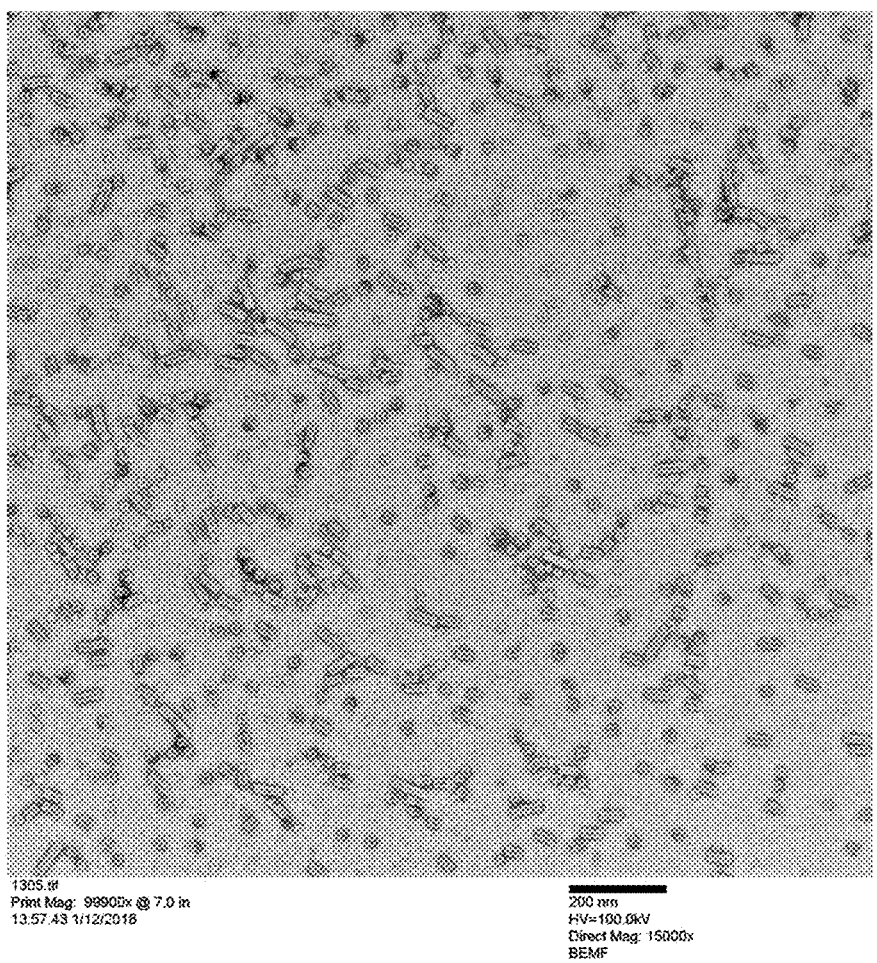

The virus filtering and inactivation effects of the MN material virus are shown in the electron micrographs of FIGS. 6a and 6b. FIG. 6a shows the TMV virus morphology before filtration, and FIG. 6b shows the TMV virus morphology after filtration. It can be seen that the TMV virus is cut into pieces by the MN material.

SARS-CoV-2 Virus Filtration Test Using MN Material

Testing Method:

1. The MN material was disinfected for 30 minutes on both sides with ultraviolet irradiation.

2. SARS-CoV-2 virus containing solution was diluted with serum-free MEM medium to 200 TCID$_{50}$/ml, 6 ml/tube, 4 tubes in total.

3. 1 ml virus solution in each tube was taken out and heated to inactivate the virus at 60° C. for 1 hour, and set aside.

4. 5 ml of the diluted virus solution was placed in a 15 ml centrifuge tube, a piece of protective fabric (MN material prepared in Example 2) was used to cover the opening of the centrifuge tube, and tied tightly with a rubber band and reinforced with a sealing film. The centrifuge tube was inverted with its opening facing downward, and placed in another sterile 50 ml centrifuge tube. The centrifuge tubes were left standing for 24 hours in a safety cabinet.

5. The next day, 20 μl of the filtrate passing through the protective fabric was collected and placed into a sterile EP tube, into which a 1 ml of 5% FBS MEM medium was added and mixed. The mixture was added to the wells of a 24-well culture plate that have been seeded with Vero cells.

6. In the same manner, 20 μl of unfiltered virus solution was drawn from within the 15 ml centrifuge tube, into which a 1 ml of 5% FBS MEM medium was added and mixed. The mixture was added add to the wells of a 24-well culture plate that have been seeded with Vero cells.

7. In the same manner, 20 μl of heat-inactivated virus solution was added into a 1 ml of 5% FBS MEM medium and mixed, and the mixture was added to the wells of a 24-well culture plate that have been seeded with Vero cells.

8. The different 24-well culture plates were incubated for 72 hours. 200 μl of culture supernatant was collected from all wells, and nucleic acids therein were extracted by magnetic bead method, and the nucleic acid level of the virus was measured by fluorescent RT-PCR.

The RT-PCR results are shown in Table 6.

TABLE 6

|  | FAM | VIC | Red |
|---|---|---|---|
| Filtrate culture | 20.49 | 17.6 | 17.51 |
| Filtrate culture | 22.1 | 19.57 | 19.44 |
| Filtrate culture | 21.29 | 18.56 | 18.29 |
| Filtrate culture | 20.48 | 17.75 | 17.55 |
| Culture of the original viral sample | 14.52 | 11.85 | 11.64 |
| Culture of the original viral sample | 14.84 | 12.54 | 12.31 |
| Culture of the original viral sample | 15.01 | 12.42 | 12.22 |
| Culture of the original viral sample | 14.89 | 12.39 | 12.19 |
| Culture of heat-inactivated viral sample | 30.94 | 28.89 | 28.72 |
| Culture of heat-inactivated viral sample | 29.78 | 27.45 | 27.51 |
| Culture of heat-inactivated viral sample | 29.51 | 27.47 | 27.37 |
| Culture of heat-inactivated viral sample | 31.6 | 29.85 | 29.76 |

According to calculation, when the concentration of the original SARS-CoV-2 viral solution was 200 TCID50/ml, after the SARS-CoV-2 virus was filtered through the protective fabric of the present disclosure for 24 h, the viral load of the filtrate was 2.0 TCID50/ml, which was about 1.0% of the original viral solution. Thus, the filtration efficiency of the protective fabric against the SARS-CoV-2 virus is 99.0%.

Radioactive Iodine-131 ($^{131}$I) self-diffusion filtration test

Test Materials:

Four materials (MN, 3M, HW, and PET) as described previously.

Test Device:

a test device containing two chambers that are separated by a filtration medium disposed therebetween.

Test Method:

1. Each of the four materials MN, 3M, HW, and PET was cut into pieces of 9 square centimeters, which was then placed in a test device containing two chambers. Each material is used as the filtration medium between the two chambers. The two chambers were initially completely closed off from each other by an impermeable barrier.

2. Medical radioactive Iodine-131 was placed in the first chamber, and heated to 35 degrees. Then the barrier between the two chambers was open, and diffusion of iodine vapor was allowed to permeate through the test material as filtration medium into the second (permeation) chamber for 60 minutes.

4. The second chamber was fast cooled, cleaned and $^{131}$I in which was collected to calculate the total adsorption capacity and radioactivity correction parameters.

The test results are shown in Table 7.

TABLE 7

| Test Material | MN | 3M | HW | PET |
|---|---|---|---|---|
| $^{131}$I initial concentration (ppb) | 1200 | 1180 | 1180 | 1230 |
| Concentration (ppb) of the source chamber after 60 minutes | 300 | 429 | 510 | 540 |

TABLE 7-continued

| Test Material | MN | 3M | HW | PET |
|---|---|---|---|---|
| Equilibrium concentration in the second chamber (ppb) after 60 minutes | 22 | 79 | 210 | 495 |
| One-way filtration efficiency | 99.08% | 96.65% | 91.10% | 79.88% |
| Corrected filtration efficiency taking account of dynamic equilibrium between the chambers | 97.56% | 89.48% | 68.66% | 28.26% |
| Filtration efficiency calculated based on radioactivity activity | 97.93% | 89.82% | 68.92% | 28.37% |

It can be seen from Table 7 that the filtration efficiency of iodine-131 of the protective fabric of the present invention is as high as 97.93%, better than other materials.

While various inventive embodiments have been described and illustrated herein, those of ordinary skill in the art will readily envision a variety of other compositions, structures, methods to obtain the results and/or one or more of the advantages described herein, and each of such variations and/or modifications is deemed to be within the scope of the invention described herein, and the appended claims.

The invention claimed is:

1. A protective fabric comprising:
   at least one structural layer comprising fibrous materials;
   a ceramic composite material layer fixed to the at least one structural layer;
   wherein the ceramic composite material layer is formed of ceramic composite material powder comprising a ceramic carrier and iron-silver crystals supported on the ceramic carrier, the iron-silver crystals comprising zero-valent iron and zero-valent silver.

2. The protective fabric of claim 1, wherein the weight ratio of the zero-valent silver to zero-valent iron in the ceramic composite material powder is 0.22:1 to 0.44:1.

3. The protective fabric of claim 1, wherein the iron-silver crystals comprise co-crystals of zero-valent iron and zero-valent silver which account for about 15% to about 85% of the total amount of iron-silver crystals.

4. The protective fabric of claim 1, wherein the iron-silver crystals are on the surface of the ceramic carrier and in the pores of the ceramic carrier.

5. The protective fabric of claim 1, wherein the ceramic composite material powder k made by: calcining a mixture containing ceramic raw material, silver citrate, and ferrous citrate under an anoxic atmosphere to thereby obtain a calcined product, wherein the ceramic raw material comprises one or both of gibbsite and alkaline sodium bentonite; and grinding the calcined product to obtain the ceramic composite material powder.

6. The protective fabric of claim 1, wherein the ceramic composite material powder is prepared by the following steps:
   mixing a ceramic raw material and water-soluble starch uniformly, and further mixing with an aqueous solution containing a mixture of silver citrate and ferrous citrate to produce a first mixture;
   granulating the first mixture to produce a first granule;
   drying, calcining and cooling the first granule in a nitrogen atmosphere to produce a second granule; and
   grinding the second granule.

7. The protective fabric of claim 1, wherein the ceramic composite material powder has a particle size smaller than 325 mesh, and a pH of not less than 10.

8. The protective fabric of claim 1, wherein the at least one structural layer comprises two structural layers each comprising fibrous materials, and the ceramic composite material layer is disposed between the two structural layers.

9. The protective fabric of claim 1, wherein the thickness of the ceramic composite material layer is between about 0.05 mm and about 3.0 mm.

10. The protective fabric of claim 1, wherein the thickness of the protective fabric is between about 0.1 mm and about 10 mm.

11. The protective fabric of claim 1, wherein the protective fabric is effective for removing or inactivating a virus.

12. The protective fabric of claim 11, wherein the virus is a coronavirus.

13. The protective fabric of claim 12, wherein the coronavirus is SARS-CoV-2 virus.

14. The protective fabric of claim 1, wherein the protective fabric is effective for suppressing bacterial growth.

15. The protective fabric of claim 1, wherein the protective fabric is effective for filtering $^{131}I$ vapor.

16. A protective product comprising a functional body made of the protective fabric of claim 1.

17. The protective product according to claim 16, wherein the protective product is protective clothing, a protective cover, a face mask, a curtain, a wall cloth, or a filtration medium for an air ventilation or circulation device.

18. A method of reducing the harm of air-borne contaminants to a person, comprising:
   the person wearing a face mask comprising the protective fabric of claim 1.

19. The method according to claim 18, wherein the air-borne contaminants comprise a coronavirus.

20. The method according to claim 19, wherein the coronavirus is SARS-CoV-2 virus.

* * * * *